(12) United States Patent
Liao et al.

(10) Patent No.: US 8,292,075 B2
(45) Date of Patent: Oct. 23, 2012

(54) HOUSING FOR A DENTAL IMPLANT

(75) Inventors: Hsin-Hsiung Liao, Wujie Township, Yilan County (TW); Mao-Sung Huang, Taichung (TW)

(73) Assignee: Mediprecision Corporation, Tucheng, Taipei County (TW)

( * ) Notice: Subject to any disclaimer, the term of this patent is extended or adjusted under 35 U.S.C. 154(b) by 114 days.

(21) Appl. No.: 12/729,468

(22) Filed: Mar. 23, 2010

(65) Prior Publication Data

US 2010/0236947 A1 Sep. 23, 2010

Related U.S. Application Data

(60) Provisional application No. 61/162,363, filed on Mar. 23, 2009.

(51) Int. Cl.
*A61B 17/06* (2006.01)
(52) U.S. Cl. .................................................. 206/438
(58) Field of Classification Search .............. 206/63, 206/528, 363, 368, 369, 773, 219, 222, 775, 206/234, 63.5, 438; 433/97, 172–176
See application file for complete search history.

(56) References Cited

U.S. PATENT DOCUMENTS

| 343,534 | A | * | 6/1886 | Eltreich | 206/234 |
|---|---|---|---|---|---|
| 5,558,230 | A | * | 9/1996 | Fischer et al. | 206/570 |
| 5,755,575 | A | * | 5/1998 | Biggs | 433/173 |
| 5,961,330 | A | * | 10/1999 | Hanson | 433/173 |
| 5,996,779 | A | * | 12/1999 | Klardie et al. | 206/63.5 |
| 6,142,296 | A | * | 11/2000 | Klardie et al. | 206/63.5 |
| 7,344,023 | B2 | * | 3/2008 | Painsith et al. | 206/234 |
| 2004/0112781 | A1 | * | 6/2004 | Hofverberg et al. | 206/438 |
| 2007/0295620 | A1 | * | 12/2007 | Collet et al. | 206/63.5 |

* cited by examiner

*Primary Examiner* — Jacob K Ackun
*Assistant Examiner* — Jenine Pagan
(74) *Attorney, Agent, or Firm* — Thomas, Kayden, Horstemeyer & Risley, LLP

(57) ABSTRACT

A housing for accommodating a dental implant is disclosed. The housing comprises a first body portion and a second body portion. The first body has an open end and a pivot end opposite to the open end. The open end is adapted to receive the dental implant. The housing further comprises a pivot element which connects with the first body portion and the second body portion at the pivot ends thereof. The first body portion and the second body portion define an inner space and the second body portion is capable of rotating with respect to the first body portion along the pivot to expose the open end.

9 Claims, 4 Drawing Sheets

HOUSING FOR A DENTAL IMPLANT

This is a non-provisional application claiming the benefit of priority based on the Provisional Application No. 61/162,363 filed on Mar. 23, 2009.

CROSS-REFERENCES TO RELATED APPLICATIONS

Not applicable.

BACKGROUND OF THE INVENTION

1. Field of the Invention

The present invention provides a housing for a dental implant. In particular, the housing is assembled into one piece and can be rotatably opened for a user to access the dental implant accommodated therein.

2. Descriptions of the Related Art

In dentistry, artificial teeth, tooth caps or bridges are conventionally used to repair teeth or consolidate intertooth structures. However, this may impose on the healthy adjacent teeth. For example, to provide adequate space for receiving an artificial tooth, a tooth cap or a tooth bridge, the adjacent healthy teeth need to be cut and ground to be smaller to act as a stable support.

With the advancement of science and technologies, dental implantation technology has also been developed. Specifically, a dental implant is directly disposed into an alveolar bone to completely replace the damaged tooth. Since the dental implantation requires no additional devices and support from adjacent teeth, it is less likely to damage adjacent natural teeth and may prevent atrophy of the alveolar bone and the gum, thus maintaining the long-term health and functions of the oral cavity. Some conventional dental implants are made into screws, and are rotatably fastened into the alveolar bone during surgery. The intention is for the dental implant and the alveolar bone to be closely connected in a mechanical way at the very start of the integration to facilitate the growth of osseous tissue on the dental implant.

The dental implantation process proceeds roughly in two stages. In the first stage, a hole is drilled in the alveolar bone and a dental implant is placed therein. The gum is temporarily sutured until the osseointegration period is completed and the newly grown osseous tissue has been closely integrated with the dental implant. During the second stage, the gum is reopened to fix an abutment onto the dental implant. Obviously, to avoid being polluted, the dental implant should be well preserved and is untouchable before it is implanted into the alveolar bone.

As shown in FIG. 1, the conventional bottle-like housing 10 for accommodating the dental implant 19 is illustrated. The housing 10 comprises a body 11, a lid 13 and a frame 15. The frame 15 is utilized to hold an end of the dental implant 19 and both of the frame 15 and the dental implant 19 can be placed into the body 11 from the opening thereof. The lid 13 is utilized to be fastened onto and sealed with the body 11 at the opening. When the dentist performs the surgery, he or she has to remove the lid 13, and then take out the frame 15 without any direct touch with the dental implant 19, especially the screw portion which is going to be fastened into the alveolar. Obviously, the conventional housing 10 comprises at least three components being assembled for accommodating the dental implant 19 and is not user friendly.

In view of this, it is highly desirable in the art to provide a novel housing for accommodating the dental implant.

SUMMARY OF THE INVENTION

One objective of this invention is to provide a housing for a dental implant. The housing is integrated and manufactured in one piece. The dental implant is clipped and secured at an end of the housing. The screw portion or the contact portion for fastening into the alveolar is located within the housing. When the housing is sealed, the inner space can be formed to well preserve the dental implant. Preferably, the inner space is airtight. The handle end of the dental implant can be exposed out of the housing to be more accessible.

Another objective of this invention is to provide a housing for a dental implant. The housing can be operated in a more user-friendly manner. The dentist or the user could rotatably slide open the housing to obtain the dental implant.

The housing disclosed in this invention comprises a first body portion, a second body portion, and a pivot element. The first body portion has a first open end and a first pivot end opposite to the first open end, wherein the first open end is capable of receiving a dental implant. The second body portion has a second pivot end. The pivot element connects with the first pivot end of the first body portion and the second pivot end of the second body portion. The first body portion and the second body portion are capable of rotating with respect to the pivot element, in which an inner space for accommodating the dental implant is defined by the first body portion and the second body portion when the housing is in a closed status, whereas the first open end is exposed when the housing is in a open status.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
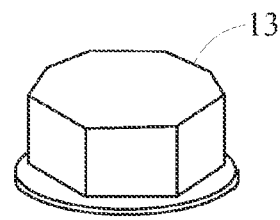
FIG. 1 is schematic views showing the conventional housing for accommodating a dental implant.
Figure 1:
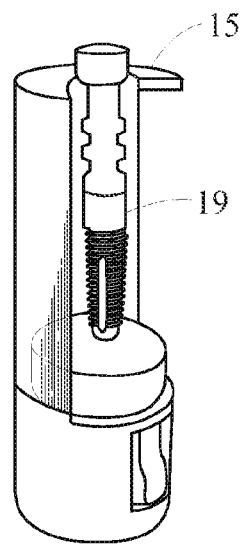
Figure 1:
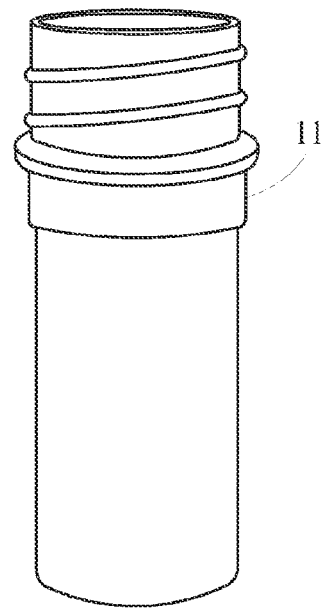
Figure 2:
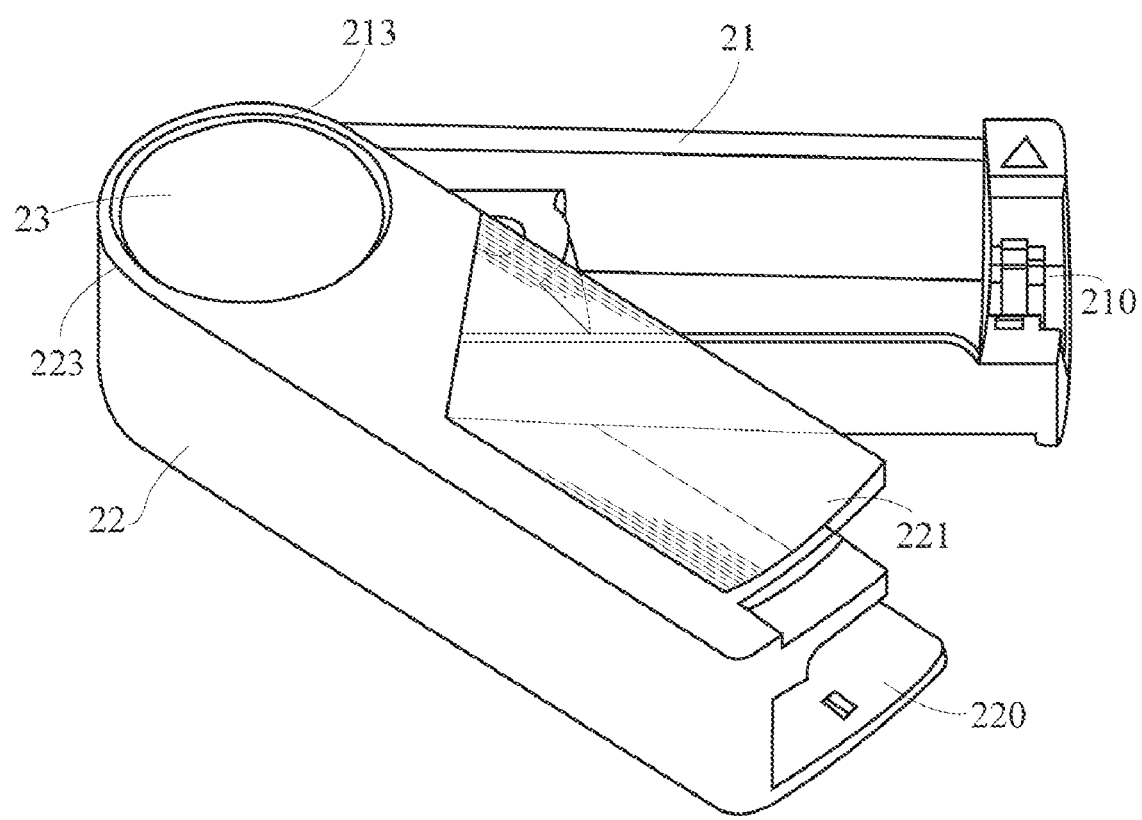
FIG. 2 is a schematic view showing the housing in accordance with this invention.

As shown in FIG. 2, a rotatable side-open type housing 20 for accommodating a dental implant is disclosed. The housing 20 mainly comprises a first body portion 21, a second body portion 22 and a pivot element 23. The first body portion 21 has two opposite ends, which are the first open end 210 and the first pivot end 213. Similarly, the second body portion 22 two opposite ends, which includes the second open end 220 and the second pivot end 223. The pivot element 23 connects with the first pivot end 213 of the first body portion 21 and the second pivot end 223 of the second body portion 22. Thus, the second body portion 22 is capable of rotating with respect to the first body portion 21 along the pivot element 23 between a closed status and an open status.

Specifically, when the housing 20 is in the closed status, the first body portion 21 and the second body portion 22 attach with each other to define an inner receiving space. Preferably, the second body portion 22 further comprises a window 221 so that the inner receiving space can be visible through the window 221. When the housing 20 is going from the closed status to the open status, the second open end 220 of the second body portion 22 departs from the first open end 210 of the first body portion 21. Due to the pivot element 23 pivoting the first body portion 21 and the second body portion 22 at the first pivot end 213 and the second pivot end 223 thereof, the second body portion 22 is capable of rotating with respect to the first body portion 21. Thus, the first open end 210 could be exposed.

Figure 3:
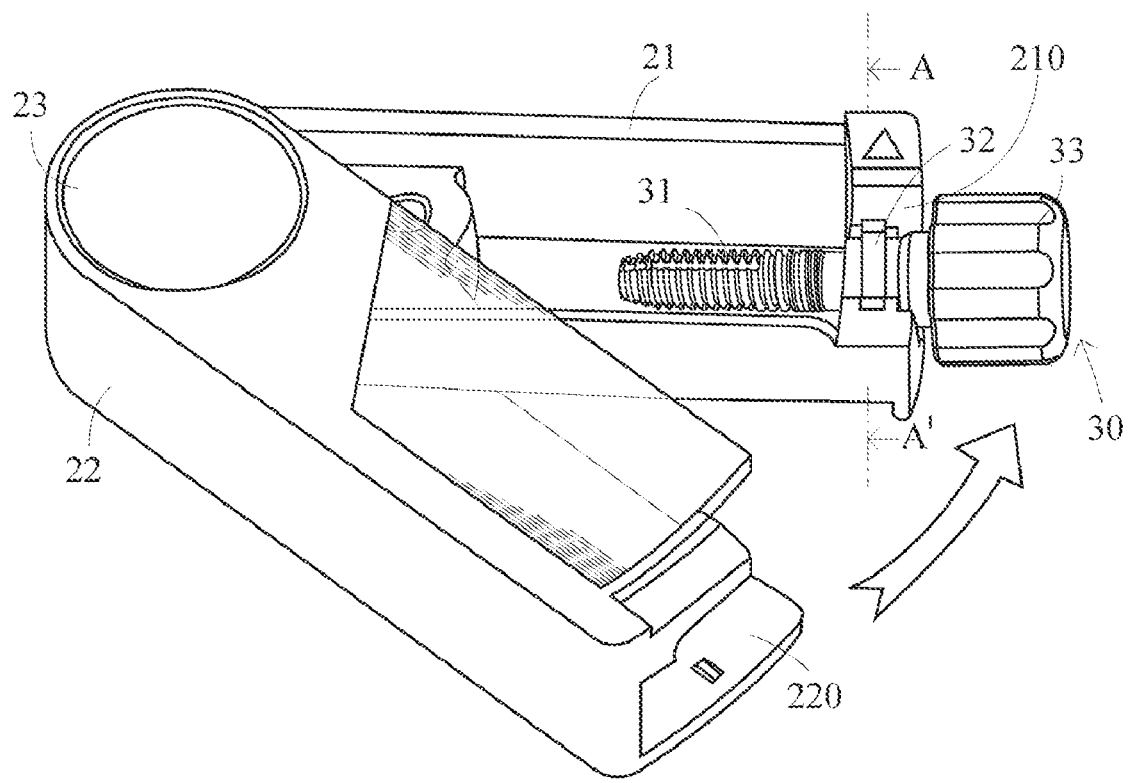
FIG. 3 is a schematic view showing the housing accommodating the dental implant in accordance with this invention.

Referring to FIG. 3, the first open end 210 can operatively receive the dental implant 30. More specifically, the dental implant 30 has an implant body 31 and a holder 32. The holder 32 of the dental implant 30 is connected with the first open end 210. Thus, the implant body 31 is well disposed in the inner receiving space without any contact with other elements. When the housing 20 is in the closed status, the second body portion 22 slides towards the first body portion 21 and the second open end 220 of the second body portion 22 is adapted to clip and secure the holder 32 within the first open end 210 of the first body portion 21. The dental implant 30 further has a handle 33, which is extended from the holder 32 and opposite to the implant body 31. When the dental implant 30 is disposed in the housing 20, the handle 33 is exposed and protruded from the housing 20. The user can remove dental implant 30 from the housing 20 by holding the handle 33.

Figure 4:
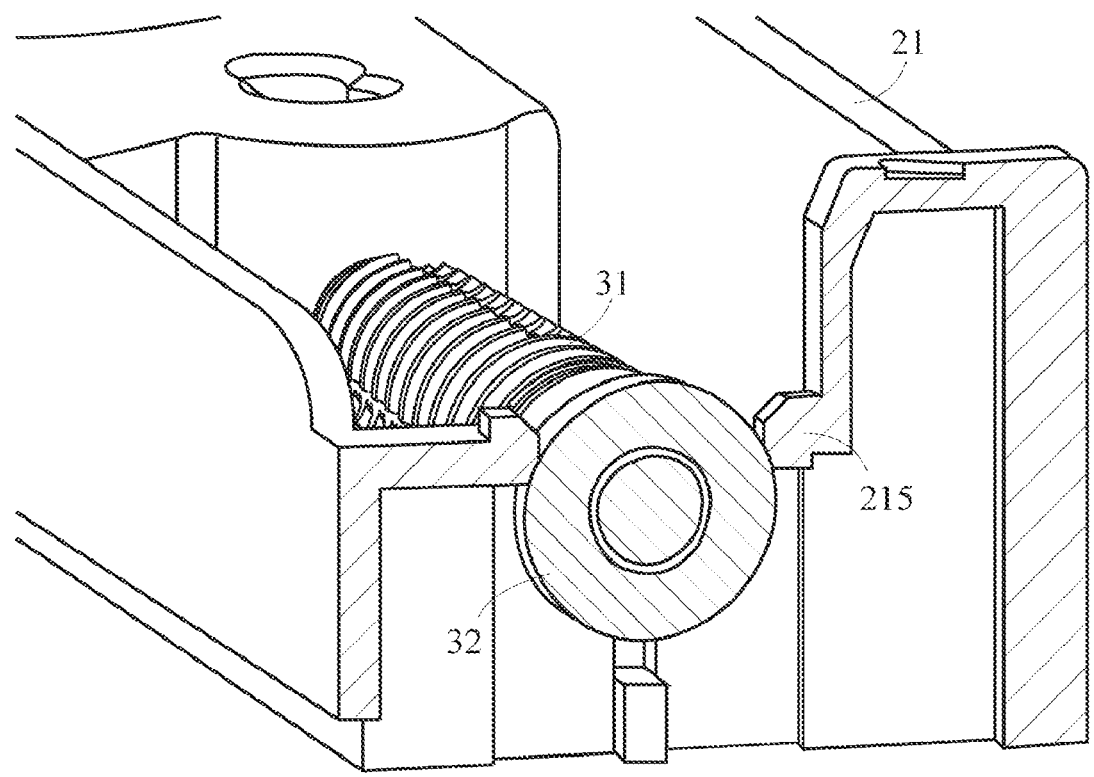
FIG. 4 is a cross-sectional view along the A-A' line of FIG. 3.

FIG. 4 is a cross-sectional view along the A-A' line of FIG. 3. The first body portion 21 further comprises a restriction structure 215 disposed at the first open end 210. The restriction structure 215 is preferably made of a plastic material or any other elastic material. Thus, the restriction structure 215 is adapted to be deformed to clip and secure the holder 32 of the dental implant 30 due to its elasticity. When the housing 20 is in the open status, the dentist or the user may hold the handle 33 and take out the dental implant 30 from the open end 210.

It is noted that, preferably, the first body portion 21 and the second body portion 22 are designed for exactly sealing with each other to form the inner receiving space in the closed status to minimize the risk of pollution to the implant body 31. Thus, sealing strips or other sealing mechanism (not shown in the figures) could be disposed on the first body portion 21 or the second body portion 22 to facilitate the inner space being sealed when the housing 20 is in the closed status. The person skilled in the art could take other manners to achieve this objective, which is not limited herein.

Given the above, the housing 20 of the present invention is manufactured in one piece to well preserve the dental implant 30 within the housing 20. The dentist or the user could open the housing 20 in a more user-friendly way to obtain the dental implant 30.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A structure comprising a housing and a dental implant, the dental implant comprising an implant body, and the housing comprising:
   a first body portion having a first open end, a first pivot end opposite to the first open end, and a restriction structure disposed at the first open end, wherein the dental implant is secured by the restriction structure;
   a second body portion having a second pivot end, and a second open end opposite to the second pivot end, wherein the second open end is capable of assembling with the first open end;
   a pivot element connecting with the first pivot end of the first body portion and the second pivot end of the second body portion;
   wherein the first body portion and the second body portion are capable of rotating with respect to the pivot element, in which an airtight inner space is cooperatively formed by the first body portion, the second body portion and the dental implant and the implant body of the dental implant is suspended in the airtight inner space when the housing is in a closed status, whereas the first open end is exposed when the housing is in a open status.

2. The structure as claimed in claim 1, wherein the dental implant further comprises a handle opposite to the implant body and a holder formed between the implant body and the handle.

3. The structure as claimed in claim 2, wherein the dental implant is connected with the first open end at the holder thereof.

4. The structure as claimed in claim 3, wherein the restriction structure secure the dental implant by clipping the holder thereof.

5. The structure as claimed in claim 2, wherein the handle is exposed when the dental implant is disposed within the housing.

6. The structure as claimed in claim 1, wherein the restriction structure is elastic so that the restriction structure is capable of being deformed to clip the holder.

7. The structure as claimed in claim 6, wherein the restriction structure is made of a plastic material.

8. The structure as claimed in claim 1, wherein the second body portion further comprises a window for enabling the inner space to be visible.

9. The structure as claimed in claim 1, further comprising sealing strips disposed on the first body portion or the second body portion to facilitate the inner space being sealed when the housing is in the closed status.

* * * * *